United States Patent [19]
Davis

[11] Patent Number: 5,246,347
[45] Date of Patent: Sep. 21, 1993

[54] INFUSION DEVICE WITH DISPOSABLE ELEMENTS

[75] Inventor: David L. Davis, San Diego, Calif.

[73] Assignee: Patients Solutions, Inc., San Diego, Calif.

[21] Appl. No.: 426,988

[22] Filed: Oct. 25, 1989

Related U.S. Application Data

[62] Division of Ser. No. 194,865, May 17, 1988, Pat. No. 5,074,759.

[51] Int. Cl.$^5$ ............................................. A61M 5/142
[52] U.S. Cl. ...................................... 417/45; 417/474; 604/31; 604/67
[58] Field of Search ............... 417/474, 475, 476, 477, 417/478, 45; 604/67, 153

[56] References Cited

U.S. PATENT DOCUMENTS

| | | | |
|---|---|---|---|
| 4,493,706 | 1/1985 | Borsanyi et al. | 604/153 |
| 4,925,444 | 5/1990 | Orkin et al. | 604/80 |
| 5,078,683 | 1/1992 | Sancoff et al. | 604/67 |

Primary Examiner—Richard A. Bertsch
Attorney, Agent, or Firm—Knobbe, Martens, Olson & Bear

[57] ABSTRACT

An infusion device with a disposable administration set which is inexpensive to manufacture. In the preferred embodiment of the present invention the disposable administration set has a plurality of elongated cam followers connected to a plate assembly, wherein the cam followers are displaced in a predetermined sequence and forced against a delivery tube by cam means driven by rotary drive means. The disposable administration set is injection molded as a single integral piece. The disposable administration set includes adjustment spacers disposed between the plate assembly and the cam followers which adjust the distance between them to keep the device accurate. In the preferred embodiment of the present invention the cam means are configured to provide fluid delivery at a consistent and uniform rate.

1 Claim, 7 Drawing Sheets

INFUSION DEVICE WITH DISPOSABLE ELEMENTS

This application is a division of application Ser. No. 194,865, filed May 17, 1988, now U.S. Pat. No. 5,074,751.

BACKGROUND OF THE INVENTION

1. Field of the Invention

This invention relates generally to a medication infusion device for administering fluid to patients and more particularly to an improved, ambulatory infusion device with a disposable administration set which is inexpensive to manufacture, convenient to operate and which ensures fluid delivery at a consistent and uniform rate.

2. Description of the Prior Art

As a result of the ongoing need for improved health care, there is a continuous effort with regard to administering intravenous fluid to patients. As is well known, medication dispensers and infusion devices are used for infusion of predetermined amounts of medication into the body of a patient. Various types of medication dispensers employing different techniques for a variety of applications are known to exist. Some existing infusion devices utilize a series of diaphragms which roll up and down inside cylinders in response to pistons located within the cylinders. Such devices, for example, as disclosed in U.S. Pat. Nos. 4,236,880, 4,277,226, 4,391,600 and 4,410,322 are characterized by relatively complicated operational procedures and numerous manufacturing and maintenance adjustments to ensure proper operation of the loading and valving functions.

Other existing infusion devices employ a finger type pump unit having fingers which are moved in predetermined sequence to squeeze a feeding tube to infuse predetermined amounts of medication continuously and cyclically into a patient. Such a prior art device is disclosed in U.S. Pat. No. 4,479,797.

In many cases it is of critical importance to provide precisely controlled and consistent flow rates of intravenous fluid to patients. This need for more controlled IV flow rates is only partially fulfilled by the above-mentioned displacement pumps. The finger type displacement pump unit as disclosed in U.S. Pat. No. 4,479,797 includes a plurality of elongate fingers which are depressed by an equal number of associated cams rotating about a shaft which is driven by a motor. A feeding tube, when placed between the fingers, is squeezed by the fingers to infuse liquid medication into a human body. The elongate fingers comprise a central finger and two side fingers arranged on either side. In such a device the side fingers completely squeeze or collapse the feeding tube at the designated point of contact on either side, and the central finger is shaped for squeezing the feeding tube and pumping medication over the length of tube between the two points, providing a pulsatile flow of fluid. During the time that the downstream side finger completely squeezes the feeding tube, while the pumping portion of the tube is filling from an upstream supply, the flow of fluid to the patient is completely obstructed.

Completely obstructing the flow of medication for periods of time and providing pulsatile flow is often a clinically unsatisfactory and undesirable condition since a patient is deprived of medication for periods of time. Additionally, fluid is delivered at non-uniform rates. Sometimes, the possibility exists at flow rates for a catheter to develop a blood clot due to lack of flow. This may also result in an occluded tubing, so that the patient may be deprived of needed medication for several hours. This condition is especially likely in a home environment which seldom has around-the-clock clinical staffing for monitoring patients. Thus, it is desirable to have an infusion device which delivers fluid to a patient at a constant and uniform rate.

Some prior art devices, in an attempt to provide non pulsatile flow of fluid, incorporate additional pulsation correction cams and cam followers. The correction cams are designed to even out overall flow from the pump through simultaneous pumping actions of multiple cams. This solution is undesirable in view of the numerous parts involved. Infusion devices utilizing piston valves and cylinders are also known to provide uniform flow; however, they do so at the expense of crude valving techniques and complex mechanisms. Thus it is desirable to have an infusion device utilizing a relatively simple technique of providing non-pulsatile flow.

As is well known, disposable equipment for medical applications is desirable so as to maintain a germ-free environment to prevent the transfer of infection especially where cost prohibits cleaning and sterilization after each use. Prior art devices employing a series of diaphragms rolling within cylinders have utilized disposable diaphragms. The disposable diaphragms, however, are flimsy and thus require a very complex loading mechanism. Prior art devices having finger type pump units, for example, as disclosed in U.S. Pat. No. 3,658,445, have only a disposable tube assembly. This has limited advantages, since the cam followers, which are not a part of the disposable assembly, are not renewed with each replacement. U.S. Pat. No. 4,479,797 disclosed other disposable elements. Since the cam followers are repeatedly flexed and fatigued as a result of being depressed by the rotating cams, it is desirable to have them renewed with every new installation to ensure proper functioning.

Thus, it is desirable to have a disposable administration set, including the pumping tube itself, a base plate against which the tube is depressed, and the cam followers. With such an arrangement, the system operates reliably and accurately over a longer period of time because its major pumping components are replace with each use. Another important consideration for disposable elements is cost, since clinical application of disposable administration sets requires that the administration sets be regularly replaced. Typically, such sets are replaced every 24 to 48 hours, and seldom remain in use longer than one week. This frequent replacement interval should ideally be fulfilled by an inexpensively molded, disposable, mechanism which would normally not last the years of service life expected from the pump itself.

Furthermore, it is desirable to have a disposable administration set which is easy to load and unload to minimize operator errors. These factors can be very important in a clinical situation when a few extra seconds may be critical to a patient's life. Typically, prior art devices require several steps to accomplish the task of loading and unloading. Additionally, it is beneficial to pinch off the delivery tube and obstruct fluid flow prior to loading or unloading the administration set.

It is also desireable to have an efficient but inexpensive occlusion detection system. Some prior art devices incorporate a pressure transducer and diaphragm assembly to monitor fluid pressure as an indication of occlusion. Such an occulsion detection technique is undesirable in view of the complexities and cost involved. Prior art devices utilizing pistons and cylinders detect occlusion by utilizing a switch mounted within the cylinder. When the pressure reaches a certain value the rotating diaphragm causes the switch to be depressed. The switch may also be mounted against the tubing such that the switch is activated when the tubing expands as a result of increased pressure due to an occlusion.

SUMMARY OF THE INVENTION

Briefly stated, the present invention is an improved, ambulatory infusion device having a disposable administration set which is inexpensive to manufacture and a pumping mechanism which provides a consistent and uniform fluid flow.

The infusion device comprises an administration set having a plurality of cam followers which are depressed in a predetermined sequence by a plurality of associated rotating cams. The cam followers squeeze a delivery tube to dispense fluid which is intravenously infused into a patient's body. The rotating cams are mounted to an axle shaft driven by a motor. The disposable administration set further comprises a plate assembly to which the cam followers are attached. The cam followers force the delivery tube against the plate assembly to pinch off the delivery tube or force fluid to flow through it. In the preferred embodiment of the present invention the administration set is advantageously disposable and inexpensive to manufacture. In accordance with one feature of the present invention the cam followers are all molded together as one piece. Alternatively, the cam followers may also be molded as one piece with the plate assembly, provided that a hinge is molded to connect the cam followers with the plate assembly. This provides a cost effective assembling technique which allows the cam followers and plate to be replaced regularly at minimal cost.

Since the cam followers are instrumental in controlling the amount of fluid dispensed, the thickness of the cam followers is a critical dimension which directly affects the degree of tube compression, and thus the cross sectional area of the delivery tube. Because some variations in thickness can be expected from one molded part to the next due to normal molding process variations, the invention utilizes gap correction spacers which counteract these thickness variations. The gap correction spacers fit between the plate and the support for the rotating cam, and thus adjust the distance between the cam and the plate. If the cam follower assembly varies in thickness, for example due to change in the pressure of an injection molding machine, both the cam followers and the gap correction spacers vary by the same amount, because they are molded as a single unit. Since an increase in thickness of the gap correction spacers results in an increase in the delivery tube gap, while an increase in the thickness of the cam followers results in a decrease in the delivery tube gap, the net effect is no change in the delivery tube gap. It is this correction technique that allows the followers to be injection molded without sacrificing the accuracy of the fluid delivery.

An additional feature of the invention allows the use of a low cost molded pressure plate assembly. Springs re used to force the face of the tubing retainer plate against the gap correction spacers. These springs, of course, must be stiff enough to be unyielding as the cams squeeze the delivery tube. By floating the plate on such springs, changes in thickness from plate to plate due to molding variations do not change the tubing gap from part to part. This is another important part of the invention which allows an easily loaded and inexpensive disposable administration set to be used without sacrificing performance or accuracy.

The plate referencing system and the gap correction spacers described above are adapted to increase the accuracy of the delivery system. In cooperation with the gap correction spacers, a channel in the pumping system receives the retainer plate and the spacers. The springs mentioned above are mounted in this channel and force the disposable assembly against a reference shoulder within the channel. This shoulder allows an easily manufactured dimensional precision to accurately define the tubing gap. The critical dimensions are the cam radius itself and the distance between the cam axis and the plate referencing shoulder. These two dimensions can be precisely controlled in the manufacturing process and they will not change significantly with time or usage.

Another feature of the present invention exists in the ability to delivery fluid at a consistent and uniform rate. The pumping mechanism includes an axle shaft and a plurality of cams mounted thereto. As the axle shaft rotates, the cams force the cam followers to squeeze the tubing and thereby displace a certain volume of fluid which is then forced out of the pump. The cams are structurally adapted such the each incremental angle of revolution displaces the same amount of fluid. This is facilitated by a non-linear cam design which provides a non-linear change in the delivery tube gap. The change in cross sectional area of the delivery tube caused by a given change in the gap depends on the tube gap at the start of the change. The cam non-linearity is designed to correlate with this change.

The present invention utilizes two pumping cams and two pumping cam followers, which function such that, at any point in time, one of the two pumping cams is always pumping. The two pumping cams comprise a primary pumping cam associated with an upstream segment of the delivery tube and a secondary pumping cam associated with a downstream segment of the delivery tube. The primary pumping cam is wider than the secondary pumping cam, so that it can displace sufficient fluid during its pumping stroke to deliver fluid external to the pump and at the same time delivery fluid to the section of the tubing beneath the secondary pumping cam to allow it to fill. The secondary pumping cam is narrower, since it only needs to delivery fluid external to the pump. The present invention additionally utilizes pinching cams and pinching cam followers, which open and close the delivery tube to allow the pumping action to function properly. The pinching cams comprise an inlet pinching cam associated with the upstream segment of the tube and an outlet pinching cam associated with the downstream segment of the tube. Thus the pumping cam followers, acted upon by the pumping cams, control the rate of fluid flow, while the pinching cam followers acted upon by the pinching cams, operate as valves for the pump. Such a configuration allows one segment of the delivery tube to fill with fluid while another segment of the delivery tube is pumping, thus providing a continuous and uniform fluid flow.

In still another feature of the present invention the disposable administration set of the infusion device is less prone to operator loading errors. This is accomplished through a reduced number of required operations and a reduction in the complexity of the operations. This is facilitated by providing channels extending along the length of the walls of a housing structure of the infusion device. These channels slidingly receive the disposable administration set in a simple, single insertion step. Additionally, since the disposable administration set includes the delivery tube retainer plate and cam followers, the position of the delivery tube relative to the tubing retainer plate and cam followers is established in a manufacturing operation which can be closely controlled. Assemblers are not under the stress of a clinical situation and they specialize the proper assembly of the disposable administration set. Good manufacturing procedures provide additional checking systems to insure that the tubing is properly loaded and that the administration set properly assembled. These practices are not possible in a clinical environment.

The pump of the infusion device is non-functional when loaded with an alien disposable administration set. Alien administration sets may have characteristics which are not suitable for safe operation of the fluid delivery system, and may operate outside of specified tolerance limits. The pump will not operate with a standard piece of delivery tube, because it requires an administration set with cam followers and a pressure plate.

Another feature of the present invention is a provision for detecting an occlusion in the downstream fluid path. The cams which squeeze the tubing are rotated by a DC motor having a predictable torque-to-current transfer function. By monitoring the current to the motor, the amount of torque required to maintain a desired cam shaft velocity can be measured. With knowledge of the motor torque required to advance the cam at each position along its rotation, against a normal fluid back-pressure, and comparing this torque with the actual measured torque, higher-than-normal pressure in the delivery tube can be sensed. If desired, a calculation can be made to determine the torque normally required to rotate the cam. This torque calculation takes into account the pressure exerted by the tue against he cam face, the effective radius of the cam-follower contact point, and the coefficient of friction of the cam-to-follower contact for each cam rotational position. This calculation is undertaken for each cam, to yield a total accumulated torque value. This total torque profile is stored in a memory device to be read out and compared with the actual torque for monitoring abnormally high pumping pressures.

Alternatively, the memory may be loaded with actual D.C. current data read during a previous operation of the pump with normal pressure. This profile is unique to the particular mechanism and instrument in which it is installed. The profile is a current waveform sampled at specific angles of revolution of the pumping system. The waveform is sampled and stored during the actual operation of the pump under controlled conditions, i.e. specific output pressure, specific temperature, etc. During later operation of the pump, these stored values are periodically compared to the actual operating current and an alarm is signalled if the difference between these two values exceeds a specified tolerance.

The control system also has access to the current operating temperature which may be used to adjust the allowable tolerance for changes in the operating temperature. The control system may also have access to data stored on the disposable administration set which indicates particular information related to manufacturing variances, such as coefficient of friction, stroke volume, tubing gap, tubing wall thickness and diameter, etc. This information may also be used to determine the appropriate alarm point. The information may be stored on the disposable administration set so that it may be read by the instrument during the sliding operation of loading the set.

The present invention uses a minimal number of parts and dissipates a minimal amount of energy. The disposable concept which includes the cam followers and the pressure plate allows for a high precision pump without complicated assembly or loading mechanisms. The set loading and retaining channels allow precise positioning of the tubing, followers, and pressure plate without any adjustments or complicated, bulky or expensive mechanisms. The disposable administration set results in an overall fluid delivery system which is small, lightweight, and ambulatory.

The design of the disposable administration set in combination with the plate referencing channels allows a sliding operation in order to laid the set. This sliding operation allows for the transfer of information from the disposable administration set to the instrument from fixed sensors. These sensors may be optical, magnetic, or some other technology. The preferred embodiment uses optical sensors to read optically coded information from a label on the administration set. This capability permits the instrument to be programmed from the information included on the label. The instrument operator is thus free from programming tasks, which would be difficult in a clinical environment. Programming information can be added to the administration set during the preparation or prescription of the medication to be delivered. The unique sliding operation makes this programming simple and cost effective in the present invention.

BRIEF DESCRIPTION OF THE DRAWINGS

The preferred embodiment of the present invention is illustrated in and by the following drawings in which like reference numerals indicate like parts and in which.

DETAILED DESCRIPTION OF A PREFERRED EMBODIMENT

Figure 1:
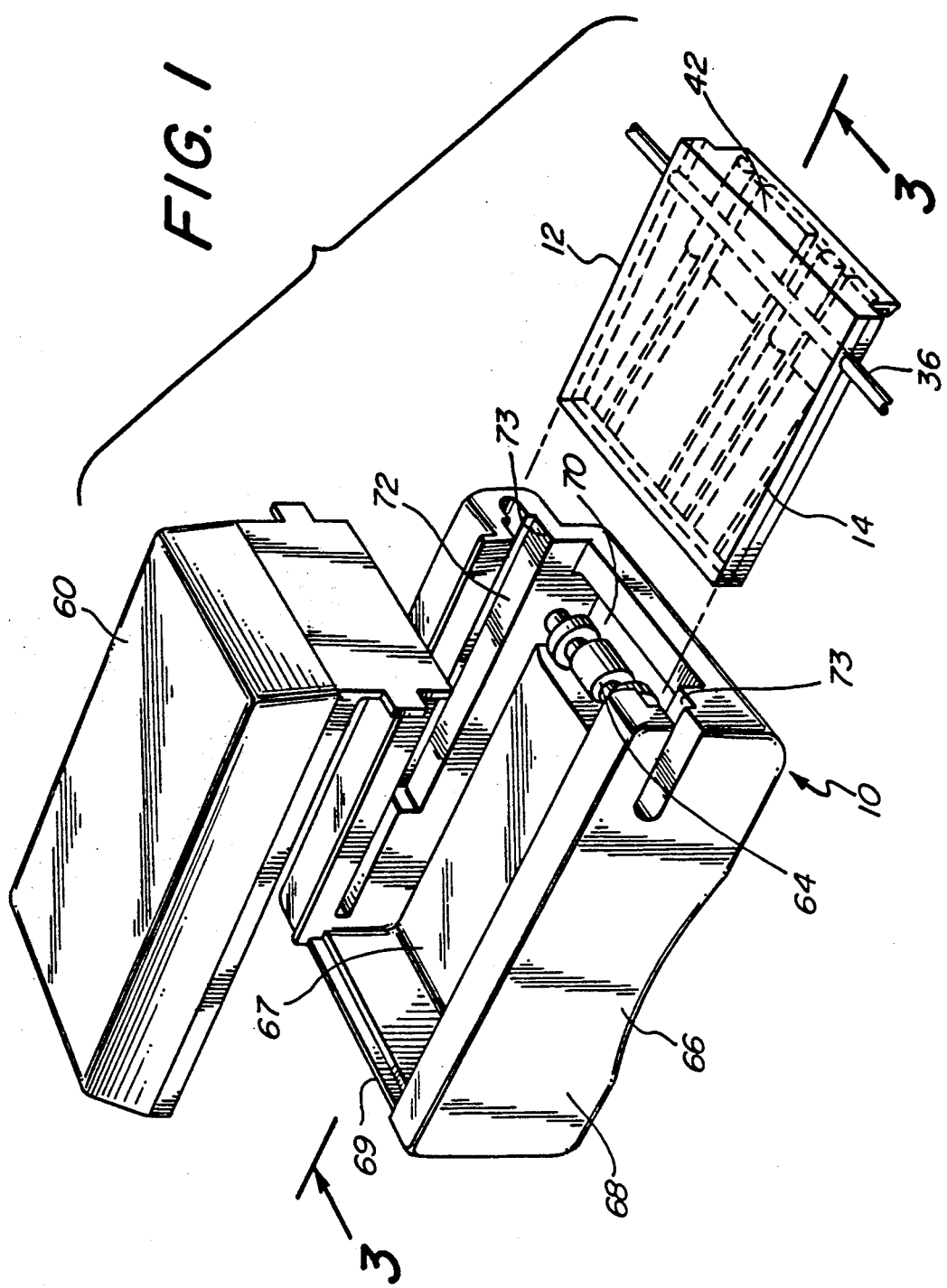
FIG. 1 is a perspective, exploded view illustrating an infusion device having a disposable administration set in accordance with the present invention, in particular showing the simple loading and unloading operation of the disposable administration set.

FIG. 1 illustrates the infusion device 10 of the preferred embodiment of the present invention for administering intravenous fluid at a consistent and uniform rate. The infusion device 10 is designed to be small, lightweight and ambulatory. The infusion device 10 includes a disposable administration set 12 having a plurality of cam followers 42 which are displaced in a predetermined sequence when depressed by a pumping mechanism 64 to squeeze a delivery tube 36 for dispensing fluid. The pumping mechanism 64 is driven by a commercially available motor 11 (not shown). Mounted within a housing structure 66, the disposable administration set 12 loads easily into the housing structure 66. Oriented directly above the housing structure 66 is an optional fluid reservoir 60 which provides a continuous flow of fluid to the inlet of the delivery tube 36 for dispensing and infusing fluid into a patient's body. Alternatively, the fluid delivery tube 36 may connect to an external reservoir (not shown), or the reservoir 60 may be located at other positions on the assembly.

Figure 3:
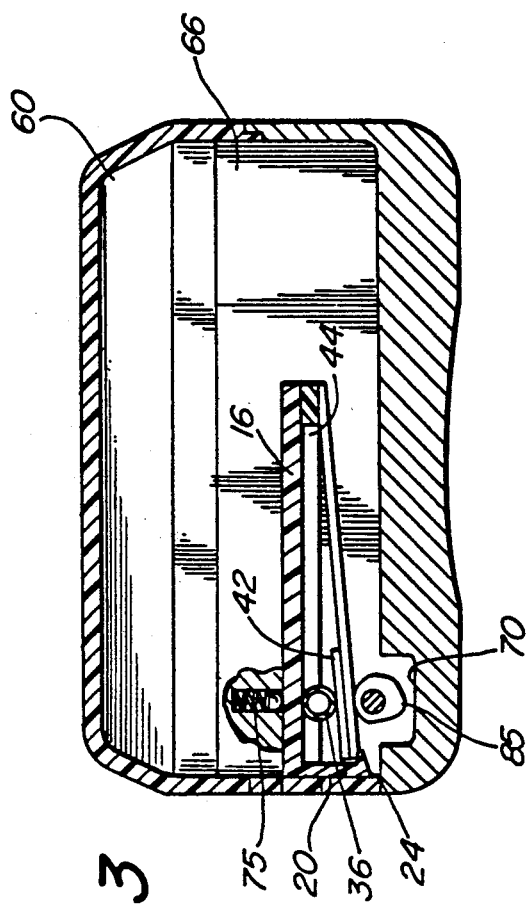
FIG. 3 is a cross section view taken along the line 3—3 of FIG. 1.

The housing structure 66 comprises a rectangular chamber 67 surrounded by side walls 68 and a rear wall 69. The floor of the rectangular chamber 67 drops into a recess 70 towards the front end. The pumping mechanism 64 is located within the recess 70. Extending throughout the length and parallel to the base of each of the side walls 68 is narrow channel 72 having a lower shoulder 73. The disposable administration set 12 slides within the channels 72. As best seen in FIG. 3, each of the channels 72 includes a spring-biased ball assembly 75. The disposable administration set 12, while being manually inserted into the channels 72, depresses the spring assemblies 75. After insertion of the set 12, the spring assemblies on either side bias the disposable administration set 12 against the shoulders 73 of the channels 72, holding the disposable administration set 12 accurately in position. In operation, the disposable administration set 12 is manually loaded into the infusion device 10 in a simple sliding operation. As the administration set 12 slides into the infusion device, the cam followers 42 are gradually pushed against the delivery tube 36 by the pumping mechanism 64.

Figure 2:
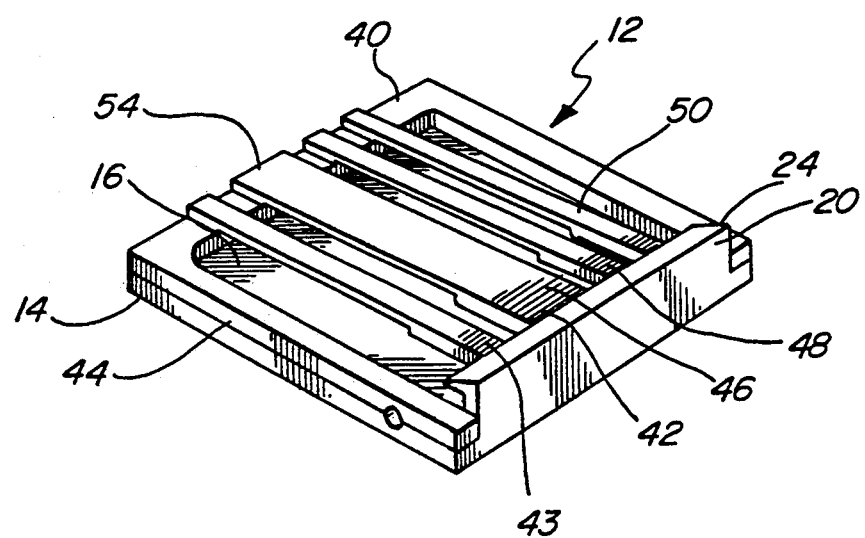
FIG. 2 is a perspective view illustrating the disposable administration set of the present invention.
Figure 6:
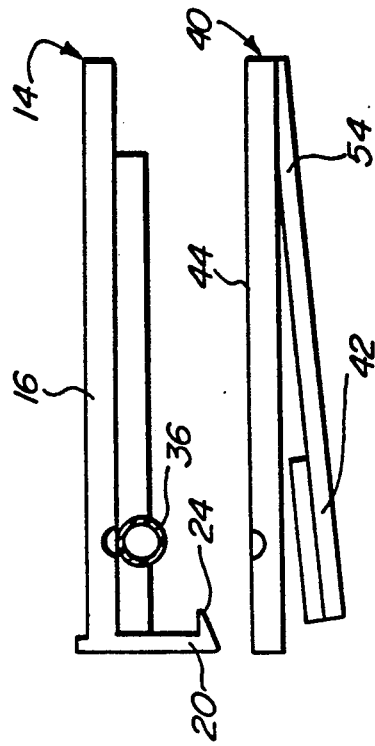
FIG. 6 is a side elevation exploded view illustrating the cam follower and spacer assembly and the plate assembly.

FIGS. 2 and 6 illustrate the disposable administration set 12 of the preferred embodiment of the present invention. The disposable administration set 12 is formed from rigid plastic or the like, and includes a tubing retainer plate assembly 14 which may advantageously be injection molded as a single piece.

The tubing retainer plate assembly 14 includes a tubing retainer plate 16 having a flat tube-contacting surface and a cam follower retainer 20 projecting normal to this surface at one end. The cam follower retainer 20 terminates in an overhanging latch 24 projecting substantially parallel to the retainer plate 16. The latch 24 serves as a locking mechanism for holding the cam followers 42 in position, adjacent the tube 36 prior to insertion of the administration set 12 into the housing 66. During insertion of the administration set 12 into the channels 72, the cam followers 42 are depressed by the pumping mechanism 64. This causes the cam followers 42 to move away from the latch 24. Thus insertion of the administration set 12 automatically moves the cam followers from a standby position, against the latch 24, to an operating position pushed against the tube 36.

Figure 5:
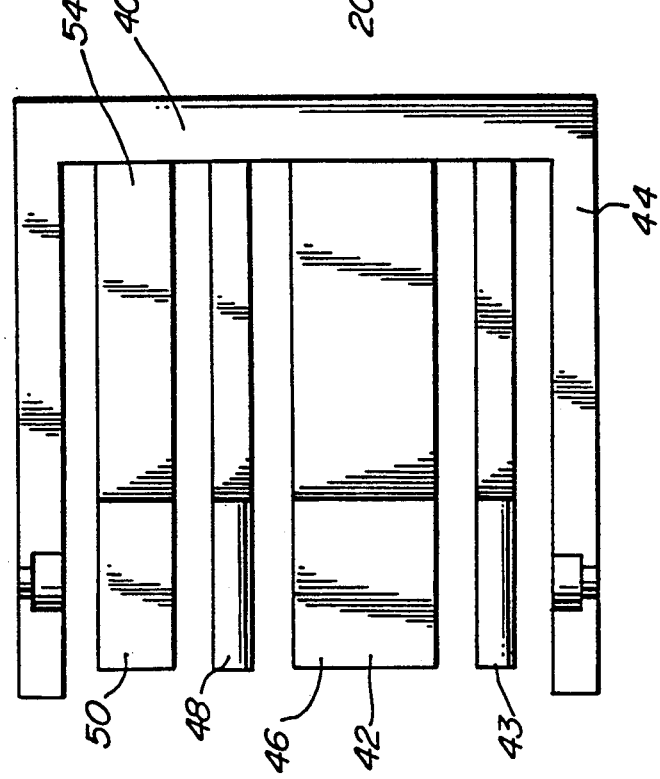
FIG. 5 is a plan view illustrating a cam follower and spacer assembly of the present invention.

As best seen in FIGS. 2, 5 and 6 the disposable administration set 12 further includes a cam follower and spacer assembly 40. In the preferred embodiment of the present invention the cam follower and spacer assembly 40 may also be injection molded as a single piece independent of the tubing retainer plate 16. Alternatively, the cam follower and spacer assembly 40 may be molded as one piece with the tubing retainer plate assembly 14 provided that a hinge is molded to connect the cam follower and spacer assembly 40 to the tubing retainer plate assembly 14. The cam follower and spacer assembly 40 includes two gap correction spacers 44 in the form of elongated extending finger-like projections which flank the tubing retainer plate 16 on either side (as best seen in FIG. 2). Since the cam followers 42 are instrumental in controlling the amount of fluid dispensed, the thickness of the cam followers 42 is a critical dimension which directly effects the volume of the delivery tube 36. The accurate pinching of the delivery tube 36 is necessary to allow a desired flow of fluid through the available passage. However, due to typical molding process variations such accuracy may not be possible. The gap correction spacers 44 advantageously counteract for these thickness variations. During the molding process, the thickness of both the cam followers 42 and the gap spacers 44 will vary by the same amount, because they are formed in the same mold cavity. Thus, any molding variations, such as those due to mold temperature or pressure, will affect both of these parts identically.

Referring to FIG. 3, it will be seen that, after insertion of the administration set 12 into the housing 6, the dispensing tube 36 is positioned immediately below the spring-biased retainer 75. The spring-biased retainer 75 holds the administration set accurately in place against the shoulders 73 (as best seen in FIG. 1) as described earlier. The cam followers 42 are pushed against the tube 36 by a plurality of cams 85, one of which is shown in FIG. 3. Pumping is accomplished, as will be described below, By squeezing the tube 36.

The gap correction spacer 44 rests between the plate 16 and the shoulder 73 (as best seen in FIG. 1). Thus, if the spacer 44 is thicker than normal, the plate 16 will be positioned further from the cam 85 than normal. However, in this case, as explained above, the cam followers 42 will also be thicker than normal, offsetting the effect of the thicker spacer 44. It is advantageous, in accomplishing this self correction, that the thickness of the spacer 44 by the same as that of the active part of the follower 42, so that they will vary identically in thickness.

The plurality of cam followers 42 as best seen in FIG. 5, includes an inlet pincher cam follower 43, a primary, upstream, inlet pumping cam follower 46, an outlet pincher cam follower 48, and a secondary, downstream, outlet pumping cam follower 50. Each of the cam followers 42 are attached to the cam follower and spacer assembly 40 by flexible cam follower arms 54. Each of the cam followers 42 are displaced toward the delivery tube 36 in a predetermined sequence. The inlet pincher cam follower 43 and the outlet pincher cam follower 48 deform the fluid delivery tube 36 to close it off, and thus act as valves. The primary pumping cam follower 46 and the secondary pumping cam follower 50 pump the fluid through the delivery tube 36. The primary pumping cam follower 46 which contacts the upstream segment of the delivery tube 36 is approximately twice the width of the secondary pumping cam follower 50, and it thus squeezes twice the length of tubing. This facilities displacement of enough fluid during a pumping stroke for delivering fluid external to the pump and at the same time delivering fluid to the downstream segment of the fluid delivery tube 36, beneath the follower 50, to allow it to fill, Thus, as the follower 46 is being advanced toward the tube 36, the follower 50 is being withdrawn. The fluid displaced by the follower 46 fills the tube 36 as it is released by the follower 50, and also supplied enough fluid to continue the outflow from the pump.

Figure 4:
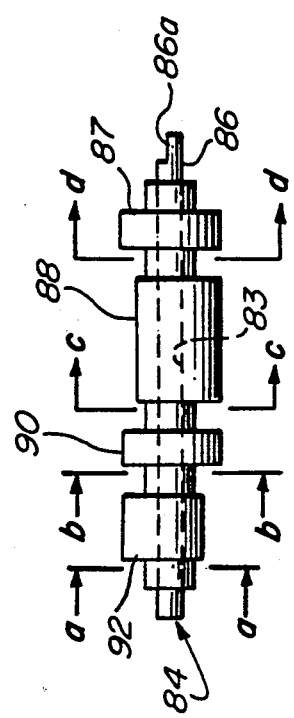
FIG. 4 is a plan view illustrating the single-piece cam of the invention.

Referring now to FIG. 4, the pumping mechanism 64 which provides a continuous and uniform flow will be describe. The pumping mechanism 64 comprises a cam assembly 84 and an axle shaft 86. In the preferred embodiment, the cam assembly 84 is preferably formed and machined from a single piece of metal. Alternatively, the cam assembly 84 may be cast, and later machined. As shown, the assembly 84 includes a central aperture 83 to accommodate an axle shaft 86. The shaft 86 may include a flat 86a to couple the shaft 86 to a motor. The axle shaft 86 rotates within bearings which are in turn mounted in two apertures formed within the walls 68 are best seen in FIG. 1. The axle shaft 86 driven by the motor provides rotation to the cam assembly 84. The cam followers 42 subsequently are displaced in a predetermined sequence, as described below, thereby squeezing the delivery tube 36 and dispensing a specified volume of fluid.

The cam assembly 84 is specifically designed such that each incremental angle of revolution displaces the same amount of fluid. The cam assembly 84 includes the plurality of spaced cams 85. The plurality of spaced cams 85 include an inlet pincher cam 87, a primary, upstream, inlet pumping cam 88 an outlet pincher cam 90 and a secondary, downstream, outlet pumping cam 92. The inlet pincher cam 87 and the primary pumping cam 88 are operably associated with the inlet pincher cam follower 43 and the primary pumping cam follower 46, respectively. Similarly, the outlet pincher cam 90 and the secondary pumping cam 92 are likewise operably associated with the outlet pincer cam follower 48 and the secondary pumping cam follower 50.

Figure 4B:
FIG. 4b is a cross section view taken along the line b—b of FIG. 4 illustrating the contour of the outlet pinching cam of the present invention.
Figure 4D:
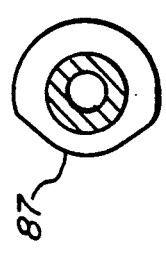
FIG. 4d is a cross section view taken along the line d—d of the present invention illustrating the contour of the inlet pinching cam of the present invention.

Referring to FIGS. 4b and 4d the inlet pincher cam 87 and the outlet pincer cam 90 are described. The inlet pincer cam 87 and outlet pincer cam 90 operate as valves for the pumping action. The surfaces of the pincher cams 87,90 are contoured such that between specified rotational positions either the upstream or the downstream segment of the tube 36 is pinched off to obstruct fluid flow.

Figure 4A:
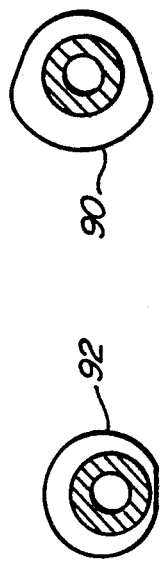
FIG. 4a is a cross section view taken along the line a—a of FIG. 4 illustrating the contour of the outlet or secondary or downstream pumping cam of the present invention.
Figure 4C:
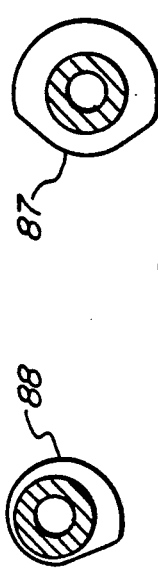
FIG. 4c is a cross section view taken along the line c—c of FIG. 4 illustrating the contour of the inlet or primary or upstream pumping cam of the present invention.

Referring to FIGS. 4a and 4c, the primary pumping cam 88 and the secondary pumping cam 92 include active pumping surfaces which are uniquely contoured so that the fluid delivery tube 36 is squeezed in such a manner that a constant speed of rotation of the axle shaft 86 results in a uniform or constant displacement of fluid volume from the appropriate segment of the fluid delivery tube 36. To accomplish this result, the primary pumping cam 88 and the secondary pumping cam 92 surfaces are contoured based upon the following principles and calculations.

The equation defining the volume of a cylindrical tube with 1 representing the length and d the inside diameter is as follows:

$$V_{cyl} = length \times area = 1 \times \pi d \times d/4$$

The equation defining the volume of an elliptical tube with g representing the inside edge diameter or minor gap and L representing the portion of the cam in contact with the cam follower is as follows:

$$V_{eli} = length \times area = 1 \times \pi \times g \times g/4 + L \times g$$

Since the circumference of the tube 36 remains relatively constant when the tubing is deformed from a cylindrical shape into an elliptical shape by the cam followers 42, the cylindrical circumference equals the elliptical circumference.

$$C_{eli} = C_{cyl}$$

Additionally the circumference of a cylinder and an ellipse are defined as $C_{cyl} = \pi d$ and $C_{eli} = 2 \times L + \pi \times g$, respectively.

Thus, since the circumference remains constant throughout the deformation process of the delivery tube 36, the two circumferences may be equated as follows:

$$\pi \times d = 2 \times L + \pi \times g$$

Solving for L $$L = (\pi \times d - \pi \times g)/2$$

and substituting for area $$area = g \times L + \pi \times g \times g/4 = g \times (\pi \times d - \pi \times g)/2 + \pi \times g \times g/4$$

$$area = (\pi/2) \times g \times d - (\pi/4) \times g \times g$$

Considering that g=d as the total area displaced and breaking that total area into 100 equal area increments $$total\ area = \pi \times d \times d/4$$

and the incremental area change $= \pi \times d \times d/400$ and then solving for the 100 g values corresponding to each of the 100 incremental area increments $$area\ 1 = (\pi/2) \times g \times d - (\pi/4) \times g \times g = \pi \times d \times d/400$$

and solving for g given the constant cylinder d value and letting $K = \pi \times d \times d / 400$ simplification
and letting $\pi/4 = c$ for simplification $$2 \times c \times d \times g - c \times g \times g - k = 0$$

and solving for the second incremental area $$2 \times c \times d \times g - c \times g \times g - 2 \times k = 0$$

and calculating the remaining 98 equal area increments.

An incremental part of the cam rotation is selected for filling and the remaining part of the rotation will be for pumping. For example, if 180° is selected for pumping, then each incremental area change will occur in 1.8° increments such that the g or the first incremental area will occur at 1.8 degrees, the g for the second incremental area will occur at 3.6 degrees, etc. Finally, the g for the 100th area will occur at 180 degrees. The cam radiuses at each increment can then be calculated by subtracting the required g value from the displacement between the center of the cam to the face of the plate assembly minus the cam follower thickness minus 2 times the tubing wall thickness plus the gap spacer thickness.

Using this derivation, it is possible to generate the proper cam pumping profile for any combination of tube diameter, cam spacing, tube wall thickness, and cam-degrees of pumping rotation.

The relationship between the cam radius and the tubing gap is algebraically proportional only when the cam radius in constant. As the cam radius changes, the effect of the approximately horizontal surface of the follower, contacting the changing cam surface makes it necessary to take the phase and amplitude into consideration. For example, a rapidly increasing cam surface results in a gap change that leads the actual radius change. Likewise, a rapidly decreasing cam radius results in a gap change that lags the actual radius change. The amount of change in phase is a function of a ratio of the beginning and ending cam radii.

The present invention utilizes approximate predicted phase changes based on calculations, of the ratio of the beginning and ending cam radii, relative to the rotational positions of the cam. This effect is more significant in the case of the rapidly changing pincher cams which are characterized by transitioning phase changes of approximately 35 degrees. Thus, once the cam profiles and approximate rotational positions of each cam are selected, the actual gaps are numerically computed as described. For each degree of rotation, each radius has a vertical component which is computed by multiplying the actual radius length by the cosine of the angle that is formed by that radius relative to a vertical line. The vertical line passes through the center of the axle shaft and is approximately normal to the surface of the cam follower. The vertical component of each radius thus changes as the cam rotates about its axis. Since the follower is formed to contact the cam surface in an approximately downward direction, for a particular degree of rotation of the cam, the cam follower will contact the cam surface at the radius which has the greatest positive vertical component. The actual radius of contact at each degree of rotation is determined by numerically computing the radius with the greatest vertical component at each degree of rotation.

Figure 7:
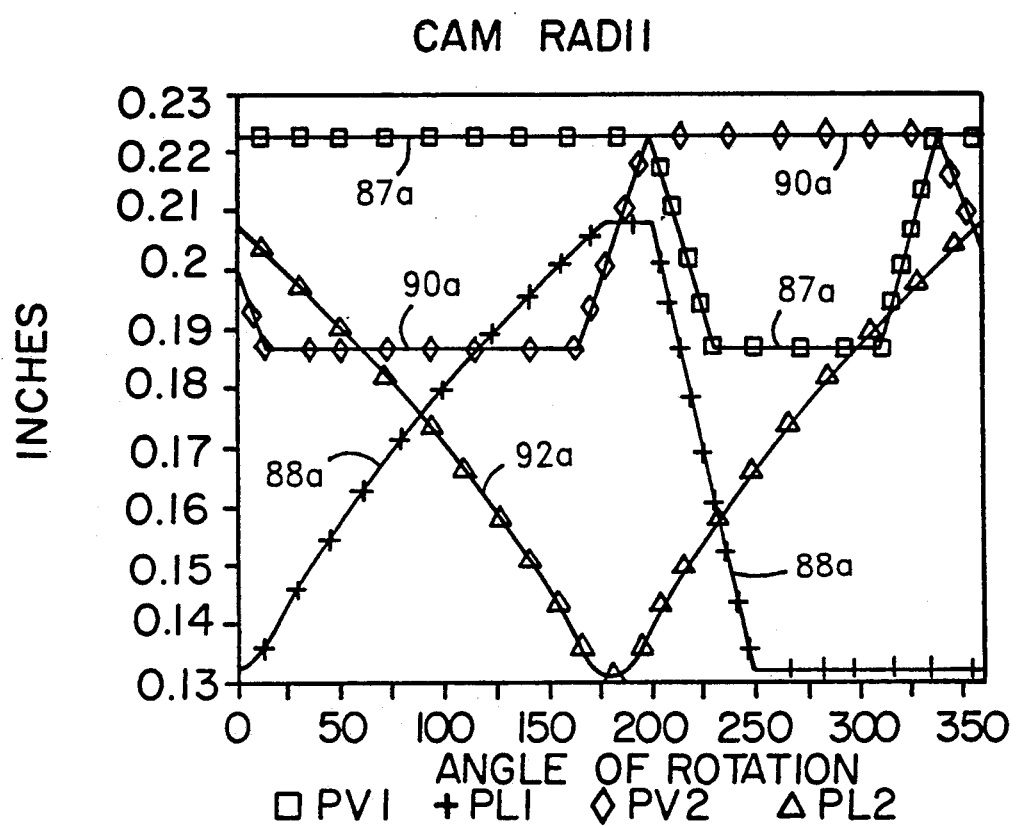
FIG. 7 is a graphical representation of the cam radii versus the angle of cam rotation of the present invention.

Referring to FIGS. 4 and 7 the operation of the cams 85 relative to the gap of the delivery tube 36 will be described. The cam assembly 84, as seen in FIG. 4, rotates about the axle shaft 86 acts through the cam followers upon the delivery tube 36 positioned directly beneath the cam assembly 84. As best seen in FIG. 7, between the rotational position 0 degrees and 200, degrees the inlet pincher cam 87, indicated by a curve trace 87a, forces the inlet cam follower 43 to pinch off the upstream segment of the tube 36 to prevent fluid flow back into the reservoir 60. While the upstream segment of the tube 36 is pinched off, the primary pumping cam 88 progresses through a gradual pumping stroke lasting from 0 degrees to approximately 175 degrees, indicated by the curve 88a. This displaces the inlet pumping cam follower 46 against the tube 36 to squeeze enough fluid to the downstream segment as well as external to the pump to continue to provide a uniform and consistent flow while the tube 36 beneath the secondary pumping cam 92 is filling. This filling is caused by a reduction in the diameter of the cam 92 through this rotational segment, as shown by curve 92a.

Once the downstream segment of the tube has been filled with fluid (at approximately the 180 degree rotation point), the outlet pincher cam 90 closes and remains closed between the rotational angles 200 degrees to 340 degrees, indicated by the curve 90a. This forces the outlet cam follower 48 to pinch off the downstream segment of the delivery tube 36. When the cam 90 pinches the tube 36 at approximately the 180 degree rotational position, the cam 87 rotates to a reduced diameter region which extends between approximately 220 degrees and 340 degrees. This opens the tube 36 beneath the cam 87, as shown by curve 87a, to allow fluid to flow from the reservoir 60 to the portion of the tube 36 which underlies the cam 88, so that this tube portion may fill. This allows the upstream segment to fill in response to a gradual reduction in the radius of the cam 88, as shown by the curve 88a between 220 degrees and 340 degrees. During this segment, the secondary pumping cam 92, indicated by the curve 92a, depresses the secondary cam follower 50 against the tube 36 dispensing fluid external to the pump.

Figure 8:
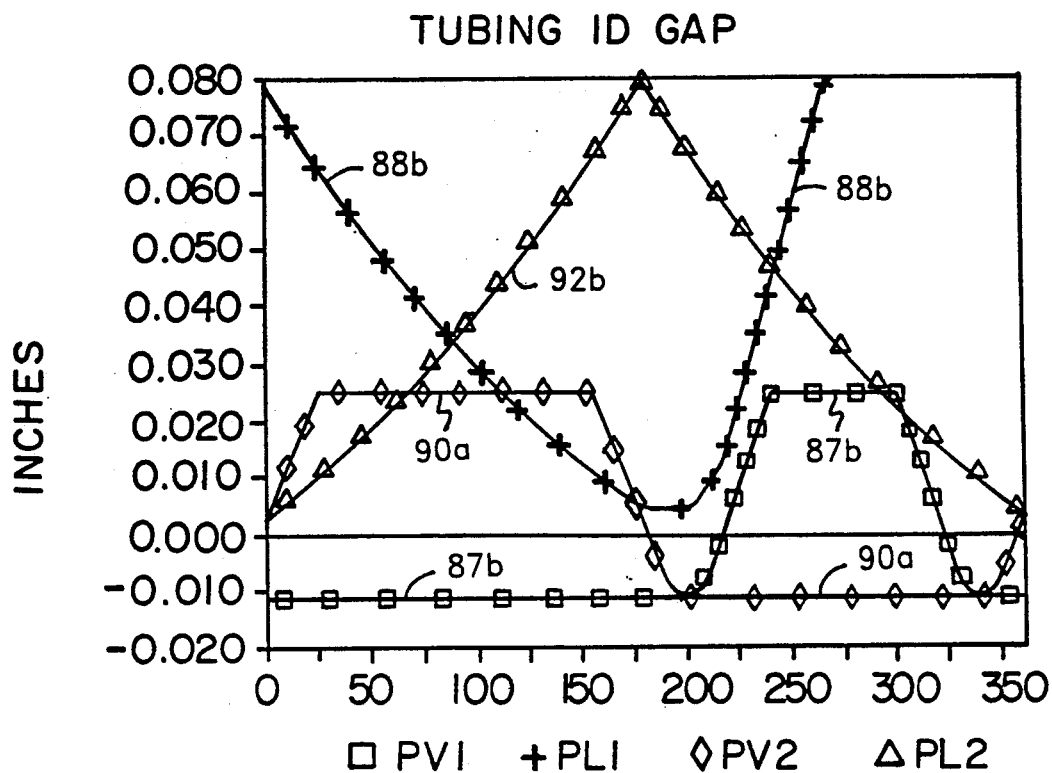
FIG. 8 is a graphical representation of the tubing ID gap versus the angle of cam rotation of the present invention.

Referring to FIG. 8, the affect of the cams 85 on the tubing gap during their rotational movement is shown. The curves of FIG. 8 are thus somewhat inversely proportional to the curves of FIG. 7, since an increase in cam radii causes a decrease in the corresponding tube gap, taking into account the fact that the gap change leads the actual radius change. The upstream segment of the tube 36, indicated by the curve 87b is completely pinched off between the rotational positions 340 degrees and 200 degrees. The primary pumping cam 88, as described above, reduces the gap beneath it to expel fluid until it reaches a rotational angle position of 175 degrees, as indicated by the curve 88b. The gap of the tube 36 beneath the cam 92 is gradually increased during this segment between 0 degrees and 180 degrees, so that the tube 36 beneath the secondary pumping cam 92 will slowly fill with fluid.

Once the downstream segment of the tube 36 has been filled, the outlet pincher cam 90 causes the downstream segment to be pinched off as indicated by the curve 90b so that the secondary pumping cam 92 can deliver fluid external to the pump. The tubing gap beneath the cam 92 varies as indicted by the curve 92b during the pumping stroke (175 degrees to 360 degrees) of the secondary pumping cam 92.

Figure 9:
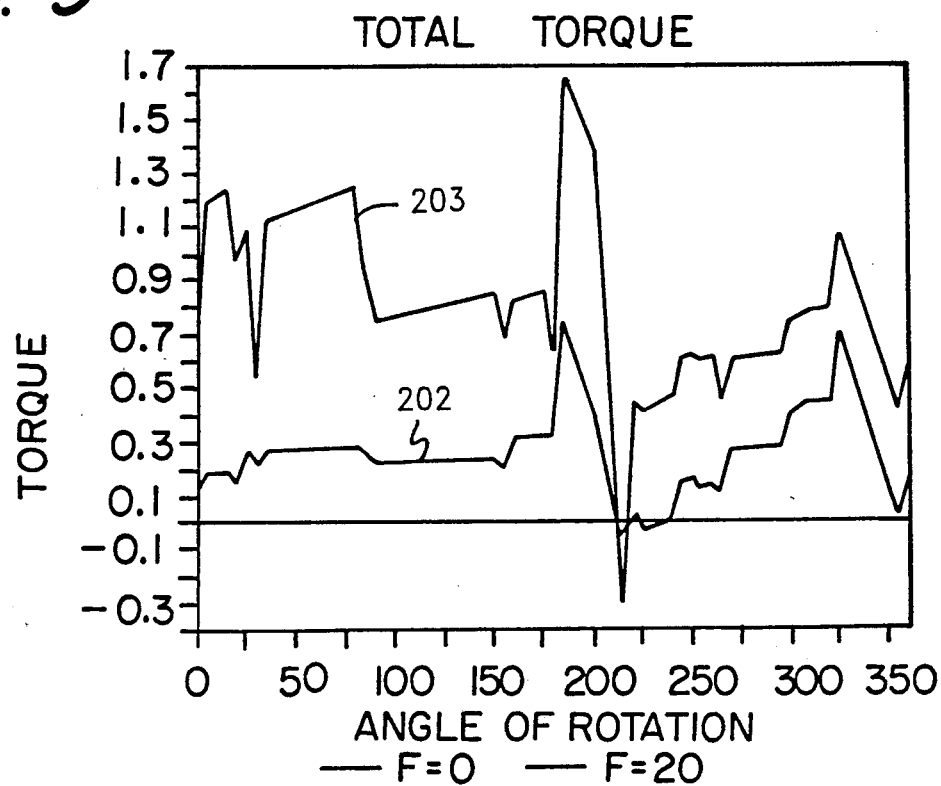
FIG. 9 is a graphical representation of the total torque versus the angle of cam rotation of the present invention.

Referring to FIG. 9, it can be seen that the total torque required from the motor to rotate the cam depends upon (1) the cam position, and (2) the back-pressure of the fluid being pumped. The lower curve 101 shows this total torque with low back pressure, while the curve 103 shows the torque required to pump at a relatively high back pressure. The curves of FIG. 9 are derived empirically, or may be calculated. In either case when the cam followers 42 have pinched off the tube 36 and actually deform the wall thickness of the tube 36, a torque spike is required. When the tube 36 is released a reverse torque spike is generated. For example, at the rotational position of 200 degrees, when both the inlet pincher cam 87 and the outlet pincher cam 90 are pressed against the tube 36, a torque spike 150 is observed. A negative spike 152 indicates the torque applied by the tube 36 as a result of the material deformation. If the cam 84 is rotated at a constant speed, the torque spikes of FIG. 9 will result in current spikes in the DC current required for motor rotation.

Figure 10:
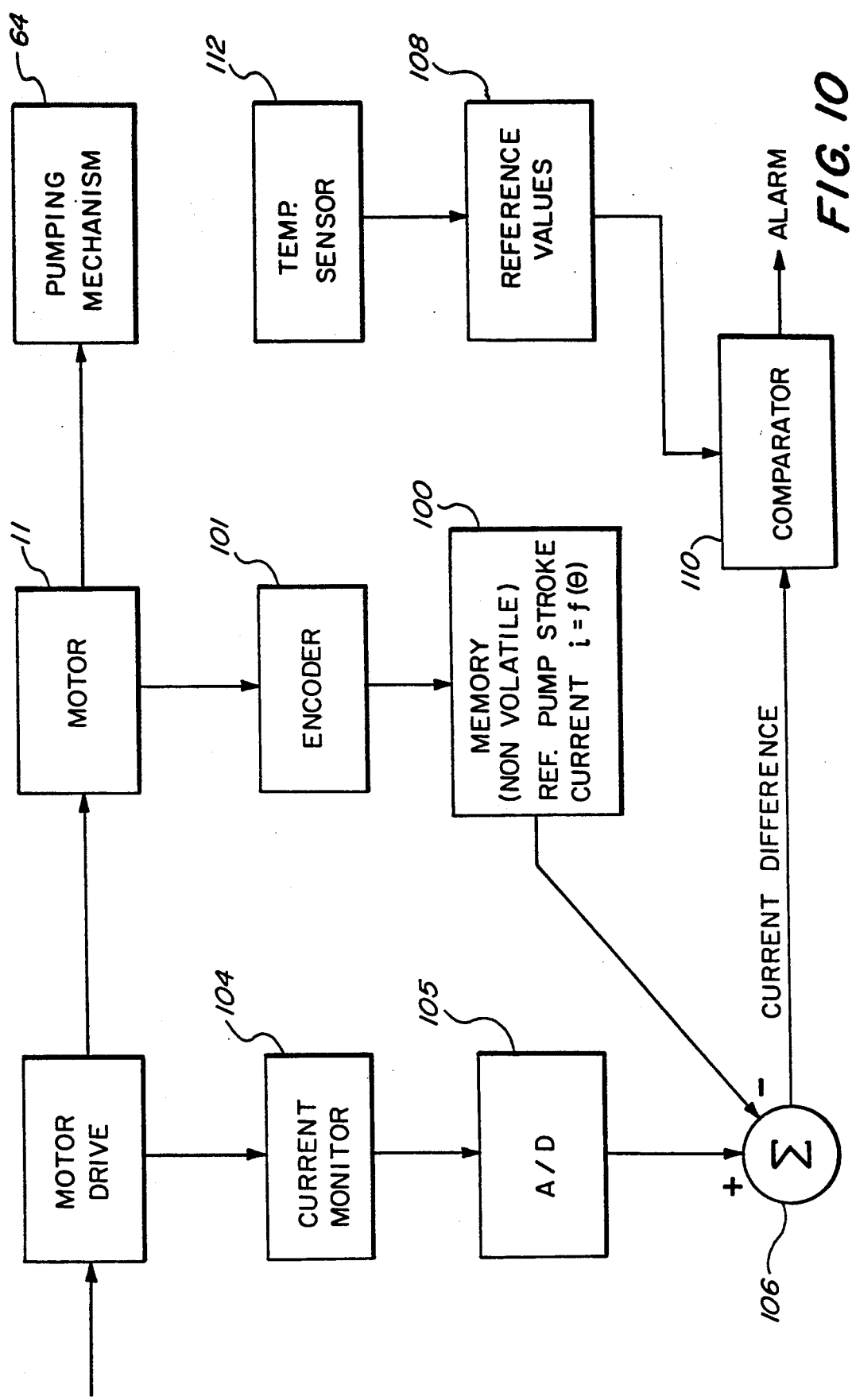
FIG. 10 is a block diagram of the occlusion detection system of the present invention.

Referring to FIG. 10, a block diagram of the occlusion detection system used in the infusion device 10 will be described. The Dc motor 11 which rotates the axle shaft 86 has a predictable torque-to-current transfer function. By monitoring the current to the motor 11 for a proportional signal thereof, the amount of torque required to maintain a constant velocity of the axle shaft 86 can be measured. With knowledge of the motor current required to advance the pumping mechanism 64 at each position along its rotation, against a normal fluid back-pressure, and comparing this current with the actual measured current, higher-than-normal pressure in the delivery tube 36 can be sensed. A calculation can be made to determine the current normally required to rotate the pumping mechanism 64. This current calculation takes into account the pressure exerted by the delivery tube 36 against the cam faces, the effective radius of the cam-to-follower contacts for each cam rotational position. This calculation is undertaken for each cam, to yield a total accumulated torque value. Alternatively, the cam can be rotated against a normal back-pressure to empirically measure the current required for normal operation. This current waveform is proportional to the torque shown in FIG. 9 as the curve 103. The current can be sensed for example at each 1 degree of rotation and stored in a memory 100. During subsequent clinical use of the pump, the actual current required to rotate the motor is monitored by a current sensor 104 and converted to digital format by an A/D converter 105 to be compared by a comparator 106 with the current profile stored in the memory device 100. A shaft encoder 101 is used to address the memory 100 to output the appropriate current level for a particular rotational position. The difference between the actual current and the stored current profile, is subsequently compared with a reference constant indicating a critical situation which is stored in memory 108. For example, the memory 108 may provide the digital equivalent for the current increase which would be expected if the back pressure increased by 5 psi. This level may indicate the likelihood that the output is occluded and an alarm should be sounded. If the error signal from comparator 106 exceeds the reference value, from the memory 108 a comparator 110 automatically may trigger an audio alarm means. The memory 108 may store plural alarm levels which are applicable at different temperatures. Thus, the allowable tolerance of the reference constant is temperature dependent. For example, temperature may affect the pliability of the delivery tube 36, in which case, the reference constant may be adjusted to allow a larger divergence between expected current and actual current when the tube is cold, and thus more rigid. Additionally, the memory 108 may store a negative threshold reference which can be compared with the error signal in the comparator 110 to sense an abnormally low actual current. Occurrence of such an abnormally low current indicates failure of the pumping system of associated abnormalities, such as failure to load a delivery tube 36 in the device. Abnormal wall thickness of the tube 36 would also be detected by an abnormal phase of the pincher current spike waveform. Additionally, damaged cam surfaces or faulty bearings or motor would contribute to abnormal behavior and thus would be detected.

In the preferred embodiment of the present invention a bar code is advantageously applied to the disposable administration set as a means of directly transferring information regarding the disposable administration set such as the pump stroke volume which relates to the amount of fluid displaced per revolution of the axle shaft, tubing diameter, or the tubing wall thickness, from the disposable administration set to the infusion device 11. This information may be, for example, directly applied to the disposable administration set during the manufacturing process. Alternatively, the bar code may provide patient and medication specific information, relating to a particular prescription being delivered, such as a dose/time specification. This information likewise may be provided by a pharmacist with the disposable administration set. Using this information, a microprocessor can easily derive an appropriate shaft velocity. The sensor may be optical, or magnetic or some other known technology.

What is claimed is:

1. A method of automatically programming a small, portable pump or cooperation with a disposable administration set comprising:
   inserting, by relative motion, said disposable administration set within said pump;
   simultaneously, automatically, transferring coded data regarding a prescribed infusion profile from said administration set to said pump, using said relative motion of said disposable administration set and said pump to automatically activate said transferring;
   In response to said transferring step, automatically storing said data in said pump; and
   automatically varying the pumping rate of said pump in accordance with said coded data regarding a prescribed infusion profile stored in said pump.

* * * * *